United States Patent
Wigal

(10) Patent No.: US 10,575,927 B2
(45) Date of Patent: *Mar. 3, 2020

(54) ORTHODONTIC APPLIANCE

(71) Applicant: Designer Ties, LLC, Hebron, OH (US)

(72) Inventor: Timothy G. Wigal, Hebron, OH (US)

(73) Assignee: Designer Ties, LLC, Hebron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/020,631

(22) Filed: Jun. 27, 2018

(65) Prior Publication Data

US 2018/0311015 A1 Nov. 1, 2018

Related U.S. Application Data

(63) Continuation of application No. 15/060,310, filed on Mar. 3, 2016, now Pat. No. 10,034,724.

(60) Provisional application No. 62/127,837, filed on Mar. 4, 2015.

(51) Int. Cl.
| | | |
|---|---|---|
| *A61C 3/00* | (2006.01) | |
| *A61C 7/12* | (2006.01) | |
| *A61C 7/30* | (2006.01) | |
| *A44C 15/00* | (2006.01) | |

(52) U.S. Cl.
CPC ............ *A61C 7/125* (2013.01); *A44C 15/007* (2013.01); *A61C 7/30* (2013.01); *A61C 7/303* (2013.01); *A61C 7/306* (2013.01)

(58) Field of Classification Search
CPC .. A61C 7/36; A61C 7/125; A61C 7/30; A61C 7/303

USPC .......................... 433/13, 15, 22, 23
See application file for complete search history.

(56) References Cited

U.S. PATENT DOCUMENTS

| | | | | | |
|---|---|---|---|---|---|
| 3,793,730 | A * | 2/1974 | Begg ........................ | A61C 7/00 433/14 |
| 3,913,228 | A * | 10/1975 | Wallshein ................ | A61C 7/00 433/18 |
| 4,585,413 | A * | 4/1986 | Wool ........................ | A61C 7/12 433/14 |
| 4,687,441 | A * | 8/1987 | Klepacki ................. | A61C 7/125 433/8 |
| 5,044,946 | A * | 9/1991 | Cleary ..................... | A61C 7/12 433/18 |
| 5,160,260 | A * | 11/1992 | Chang ...................... | A61C 7/12 433/2 |

(Continued)

FOREIGN PATENT DOCUMENTS

DE 20221191 U1 10/2005

OTHER PUBLICATIONS

European Patent Office, Extended European Search Report (European Pat. Appl. No. 16759514.9), dated Sep. 3, 2018, pp. 1-6.

*Primary Examiner* — Nicholas D Lucchesi
(74) *Attorney, Agent, or Firm* — Ice Miller LLP

(57) ABSTRACT

Various embodiments of an orthodontic appliance are provided. In one embodiment, an orthodontic appliance is provided, the appliance comprising: a body; at least one ring-shaped member connected to the body via at least one connecting portion; wherein the body and the at least one ring-shaped member are oriented adjacent to one another; and wherein the body and the at least one ring-shaped member are not coplanar when in an unloaded state.

3 Claims, 12 Drawing Sheets

(56) References Cited

U.S. PATENT DOCUMENTS

| | | | |
|---|---|---|---|
| 7,204,691 B2* | 4/2007 | Darling | A61C 7/303 433/11 |
| 7,306,458 B1* | 12/2007 | Lu | A61C 7/14 433/16 |
| 2004/0053188 A1* | 3/2004 | Callabe | A61C 7/282 433/19 |
| 2006/0046223 A1 | 3/2006 | Abels et al. | |
| 2006/0257808 A1* | 11/2006 | Feller | A61C 7/00 433/2 |
| 2006/0292517 A1* | 12/2006 | Smith | A61C 7/00 433/13 |
| 2007/0128572 A1* | 6/2007 | Herman | A61C 7/00 433/23 |
| 2010/0129765 A1* | 5/2010 | Mohr | A61C 7/12 433/10 |
| 2012/0129119 A1* | 5/2012 | Oda | A61C 7/30 433/11 |
| 2015/0202075 A1* | 7/2015 | Vincent | A61C 7/08 128/848 |

* cited by examiner

ORTHODONTIC APPLIANCE

CROSS-REFERENCE TO RELATED APPLICATIONS

This application is a continuation of U.S. patent application Ser. No. 15/060,310, filed Mar. 3, 2016, which claims the priority benefit of U.S. Provisional Patent Application No. 62/127,837, filed on Mar. 4, 2015, which are each herein incorporated by reference in their entirety.

BACKGROUND

Perhaps as many as 70% of U.S. teenagers, as well as many adults, currently use, or have used, dental braces. Traditional braces include brackets affixed to teeth, and archwires configured to extend through slots in the brackets. The archwires are traditionally attached to the brackets via ligatures or o-ties. Each of these elements are also referred to generally as "orthodontic appliances."

Many individuals wish to customize or decorate their braces. However, customization of these orthodontic appliances is limited to changing the colors, specifically of the ligature or o-tie portions of the appliance. For instance, an individual may want to include ligatures or o-ties matching her/his favorite color, her/his school's colors, and the like. Individuals have no other readily available means by which to modify their orthodontic appliances, absent permanent modification of the appliances.

What is needed is an orthodontic appliance including a surface for displaying shapes, textures, patterns, letters, numbers, symbols, indicia, colors, and the like to enable a user of braces gain the ability to customize them.

SUMMARY

In one embodiment, an orthodontic appliance is provided, the appliance comprising: a substantially planar body; at least one ring-shaped member connected to the substantially planar body via at least one connecting portion; wherein the substantially planar body and the at least one ring-shaped member are oriented adjacent to one another; and wherein the substantially planar body and the at least one ring-shaped member are not coplanar when in an unloaded state.

In another embodiment, an orthodontic appliance is provided, the appliance comprising: a substantially planar body; at least one ring-shaped member connected to the substantially planar body via at least one connecting portion; and wherein the substantially planar body and the at least one ring-shaped member are substantially parallel.

In another embodiment, an orthodontic appliance is provided, the appliance comprising: a substantially planar body; at least one ring-shaped member connected to the substantially planar body via at least one connecting portion; wherein the substantially planar body and the at least one ring-shaped member are substantially parallel; wherein the substantially planar body and the at least one ring-shaped member are not coplanar when in an unloaded state; and wherein the substantially planar body has a width and length greater than the width and length of the at least one ring-shaped member and at least one connecting portion.

In another embodiment, an orthodontic appliance is provided, the appliance comprising: a body; at least one ring-shaped member connected to the body via at least one connecting portion; wherein the body and the at least one ring-shaped member are oriented adjacent to one another; and wherein the body and the at least one ring-shaped member are not coplanar when in an unloaded state.

In another embodiment, an orthodontic appliance is provided, the appliance comprising: a body; at least one ring-shaped member connected to the body via at least one connecting portion; and wherein the body and the at least one ring-shaped member are substantially parallel.

In another embodiment, an orthodontic appliance is provided, the appliance comprising: a body; at least one ring-shaped member connected to the body via at least one connecting portion; wherein the body and the at least one ring-shaped member are substantially parallel; wherein the body and the at least one ring-shaped member are not coplanar when in an unloaded state; and wherein the body has a width and length greater than the width and length of the at least one ring-shaped member and at least one connecting portion.

BRIEF DESCRIPTION OF THE DRAWINGS

The accompanying figures, which are incorporated in and constitute a part of the specification, illustrate various example configurations, and are used merely to illustrate various example embodiments. In the figures, like elements bear like reference numerals.

DETAILED DESCRIPTION

Figure 1A:
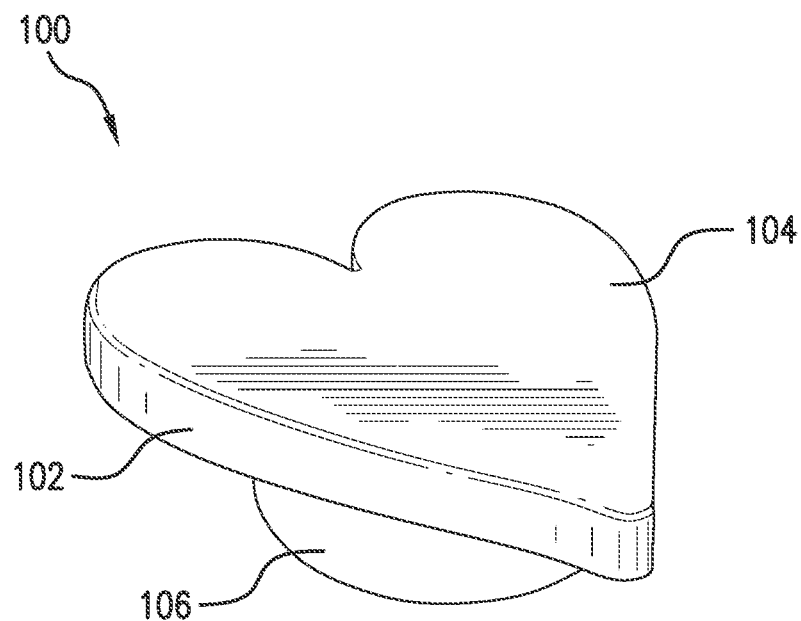
FIG. 1A illustrates a perspective view of an example embodiment of an orthodontic appliance.
Figure 1B:
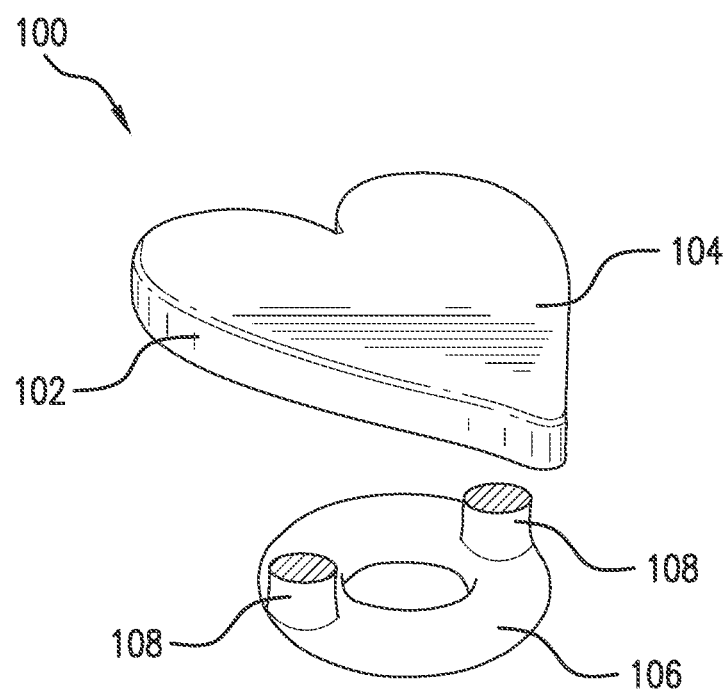
FIG. 1B illustrates an exploded perspective view of an example embodiment of the orthodontic appliance.

FIGS. 1A and 1B illustrate an example embodiment of an orthodontic appliance 100. Appliance 100 may include a body 102. Body 102 may include a surface 104. Body 102 may be operatively connected to at least one ring-shaped member 106 via at least connecting portion 108.

In one embodiment, appliance 100 may include a plurality of bodies 102.

Appliance 100 may be configured to attach an archwire to a bracket for a user wearing braces. Appliance 100 may comprise any of a variety of materials, including for example a rubber, a polymer, an alloy, a metal, an organic material, a textile, and the like. Appliance 100 may comprise an elastomeric material. Appliance 100 may include a resilient material. Appliance 100 may include a silicone. Appliance 100 may include a polyurethane. Appliance 100 may include a composite material, including for example any of the materials recited above. Appliance 100 may include for example an elastomeric material in ring-shaped member 106, and a polymer material in body 102. Appliance 100 may include a rigid material. For example, at least a portion of body 102 may include a rigid material.

Body 102 may be substantially planar. Body 102 may include a substantially planar surface 104. Body 102 may be substantially non-planar. Surface 104 may be substantially non-planar. Body 102 and/or surface 104 may include a curvature, undulations, and the like. Body 102 may be domed.

Body 102 may include any of a variety of decorative features. Body 102 may include a decorative shape, such as a heart as illustrated in FIGS. 1A and 1B. Body 102 may include any of a variety of shapes, including for example any geometric shape such as a circle, a square, a rectangle, a triangle, a pentagon, a hexagon, and the like. Body 102 may include an image. Body 102 may include a smiley face shape, including for example cutouts, raised portions, indentations, and the like to make up the eyes and/or mouth of the shape. Body 102 may include a letter shape, number shape, or other common symbol shape, including for example a punctuation mark or other indicia. Body 102 may include a logo shape, including for example a logo of a sport, sports team, ball, business, and the like. Body 102 may include a flag shape. Body 102 may include a star shape. It is contemplated that body 102 may include literally any shape desirable by a user, with a user's imagination being the only limitation.

Body 102 may include any of a variety of colors, including solid colors, patterned colors, random colors, the same colors as the remainder of appliance 100, different colors from the remainder of appliance 100, and the like.

Body 102 may be substantially solid. Body 102 may include one or more perforation, aperture, slit, indentation, striation, and the like as necessary for achieving the intended design and appearance of appliance 100.

Body 102 may include any of a variety of decorative objects, including for example: a gem, mineral, or other stone such as a diamond or the like; a polymer or glass replica of a gem, mineral, or other stone; a metallic object in any of a variety of shapes, textures, colors, and the like, such as a gold or silver decoration; an LED light; an electronic display; and the like. Body 102 may be any of a variety of jewelry items.

Body 102 may have any of a variety of dimensions. Body 102 may have a thickness ranging between about 0.1 mm and about 5.0 mm. Body 102 may have a thickness of about 1.0 mm. Body 102 may have a width and length ranging between about 1.0 mm and about 10.0 mm. Body 102 may have a width and length of about 5.0 mm. Body 102 may have a width and length that is greater than the width and length of the remainder of appliance 100. Body 102 may have a width and length that is greater than the width and length of a bracket (not shown) to which appliance 100 is attached. Body 102 may at least partially conceal the remainder of appliance 100 and/or a bracket (not shown) when appliance 100 is installed.

It is understood that the size and shape of body 102 is not restricted in any manner by the size and shape of a bracket (not shown) to which appliance 100 is applied. That is, the design of appliance 100 permits body 102 to cover as much, or as little, of at least one ring-shaped member 106 and at least one connecting portion 108 as desired.

Any of the various elements, including colors, symbols, letters, numbers, shapes, jewelry, and the like described above may be applied specifically to surface 104 rather than to body 102 generally. Surface 104 may include a printed image. Surface 104 may include a printed photograph. Surface 104 may include the distal-most portion of appliance 100. At least one ring-shaped member 106 may be the proximal-most portion of appliance 100. Surface 104 may be oriented substantially opposite at least one ring-shaped member 106. In one embodiment, surface 104 may serve as a plane upon which one may write, color, draw, engrave, adhere, and the like, any symbol, number, letter, design, indicia, etc. that one desires.

At least one ring-shaped member 106 may be substantially annular in shape. At least one ring-shaped member 106 may but substantially elastic. At least one ring-shaped member 106 may be substantially resilient. At least one ring-shaped member 106 may be configured to extend below the wings of a bracket (not shown), but above an archwire (not shown), thus selectively attaching the archwire to the bracket. At least one ring-shaped member 106 may include a color, pattern, or design substantially similar to the remainder of appliance 100. At least one ring-shaped member 106 may include a color, pattern, or design substantially different from the remainder of appliance 100.

At least one ring-shaped member 106 may be oriented substantially parallel to body 102. At least one ring-shaped member 106 may be oriented substantially parallel to surface 104. At least one ring-shaped member 106 may be oriented in a non-parallel arrangement relative to body 102. At least one ring-shaped member 106 may be oriented in a non-parallel arrangement relative to surface 104.

At least one ring-shaped member 106 may have an unloaded outer diameter between about 1.0 mm and about 10.0 mm. At least one ring-shaped member 106 may have an unloaded outer diameter of about 3.0 mm. At least one ring-shaped member 106 may have an unloaded inner diameter between about 0.5 mm and about 9.0 mm. At least one ring-shaped member 106 may have an unloaded inner diameter of about 1.0 mm. At least one ring-shaped member 106 may have an unloaded thickness between about 0.1 mm and about 5.0 mm. At least one ring-shaped member 106 may have an unloaded thickness of about 1.0 mm.

At least one ring-shaped member 106 may be attached to body 102 via at least one connecting portion 108. At least one connecting portion 108 may extend substantially orthogonally to at least one ring-shaped member 106. At least one connecting portion 108 may extend substantially orthogonally to body 102. At least one connecting portion 108 may extend substantially orthogonally to surface 104. In one embodiment, at least one ring-shaped member 106 and body 102 are substantially parallel, and at least one connecting portion 108 extends between at least one ring-shaped member 106 and body 102 and is substantially orthogonal to each.

At least one ring-shaped member 106 and body 102 may be substantially parallel while not being coplanar when unloaded. When unloaded, at least one ring-shaped member 106 and body 102 may be in separate planes separated by a distance between about 0.2 mm and about 5.0 mm. When unloaded, at least one ring-shaped member 106 and body 102 may be in separate planes separated by a distance of about 0.8 mm.

At least one connecting portion 108 may be configured to stretch or otherwise deform so as to permit variation in the separation of body 102 and ring-shaped member 106 as may be necessary during installation or use of appliance 100, or as a result of variation in dimension of brackets (not shown) to which appliance 100 may be applied. At least one connecting portion 108 may be stretched or otherwise deformed without significantly deforming body 102, such that body 102 may remain substantially planar.

Appliance 100 may be manufactured in a variety of manners. For example, at least one portion of appliance 100 may be injection molded into a mold. At least one portion of appliance 100 may be assembled from parts that are fastened to one another via any known fastening means, including for example via an adhesive or polymer welding. At least one portion of appliance 100 may be carved or machined out of a section of billet material. At least one portion of appliance 100 may be printed using a three-dimensional printer.

Figure 2A:
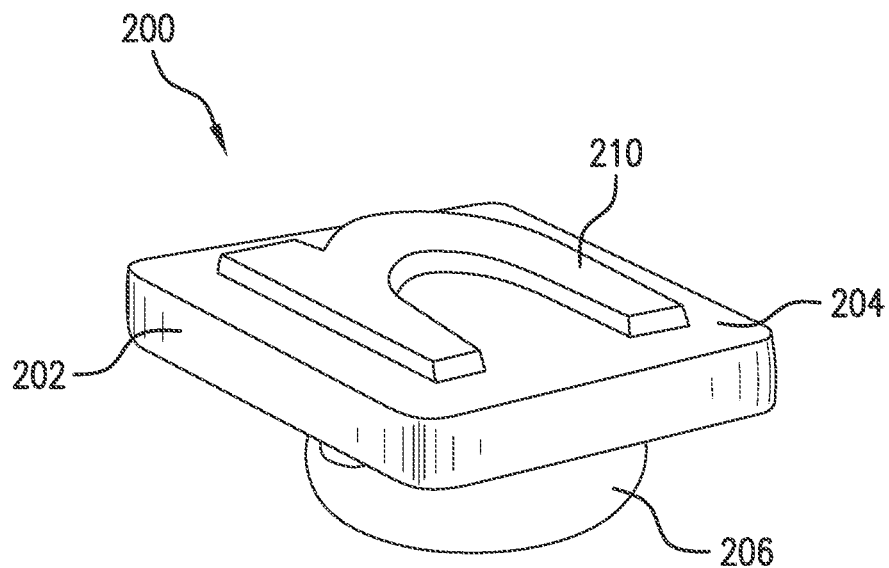
FIG. 2A illustrates a perspective view of an example embodiment of an orthodontic appliance.
Figure 2B:
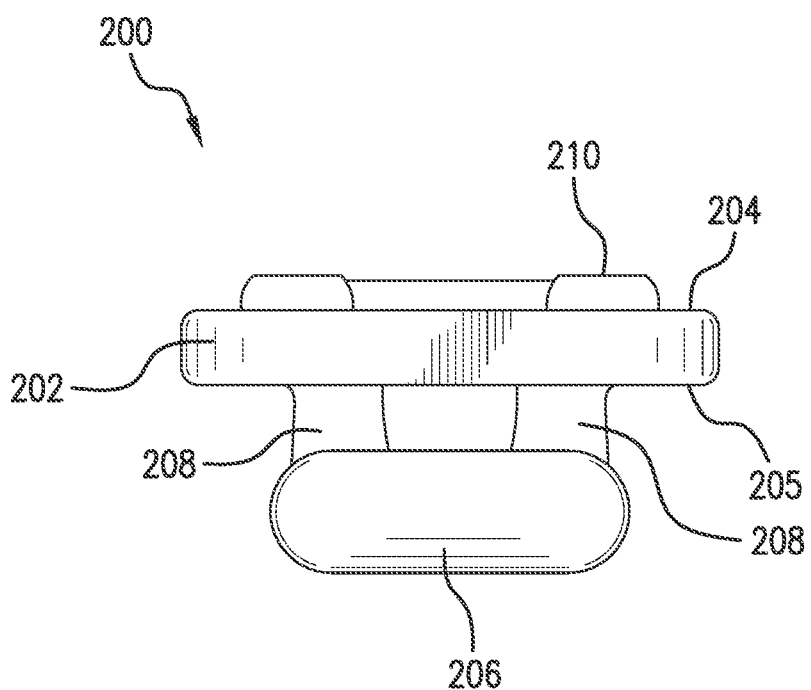
FIG. 2B illustrates an elevational view of an example embodiment of the orthodontic appliance.

FIGS. 2A and 2B illustrate an example embodiment of an orthodontic appliance 200. Appliance 200 may include a body 202. Body 202 may include a surface 204. Body 202 may include an inner surface 205. Body 202 may be operatively connected to at least one ring-shaped member 206 via at least connecting portion 208. Surface 204 may include a raised element 210.

Body 202 may be substantially planar. Body 202 may be substantially non-planar. Surface 204 may be substantially planar. Surface 204 may be substantially non-planar.

Raised element 210 may form any of the variety of symbols, letters, numbers, shapes, logos, indicia, and the like described above with respect to FIGS. 1A and 1B. Raised element 210 may include a color that is different from the remainder of surface 204. Raised element 210 may be a border.

Figure 2C:
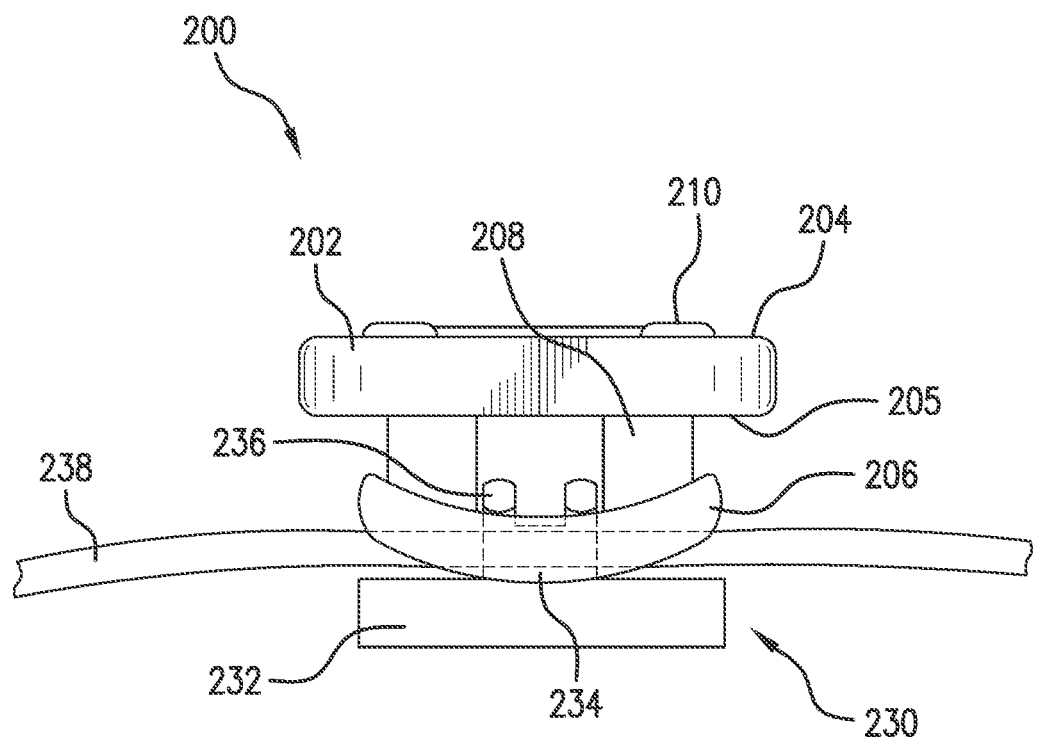
FIG. 2C illustrates an elevational view of an example embodiment of the orthodontic appliance interacting with a bracket and an archwire.

FIG. 2C illustrates an appliance 200 interacting with a bracket 230 and an archwire 238. Bracket 230 may include a base 232. Bracket 230 may include a stanchion 234. Bracket 230 may include at least one wing 236. In practice, archwire 238 may be oriented in a slot in bracket 230, after which at least one ring-shaped member 206 is oriented below at least one wing 236 and above archwire 238 so as to selectively arrest archwire 238 within the slot. The at least one ring-shaped member 206 may be stretched into place, such that it is in a state of tension upon application to the bracket. In this manner, appliance 200 may maintain itself firmly in position until removal of it is desired.

Figure 3:
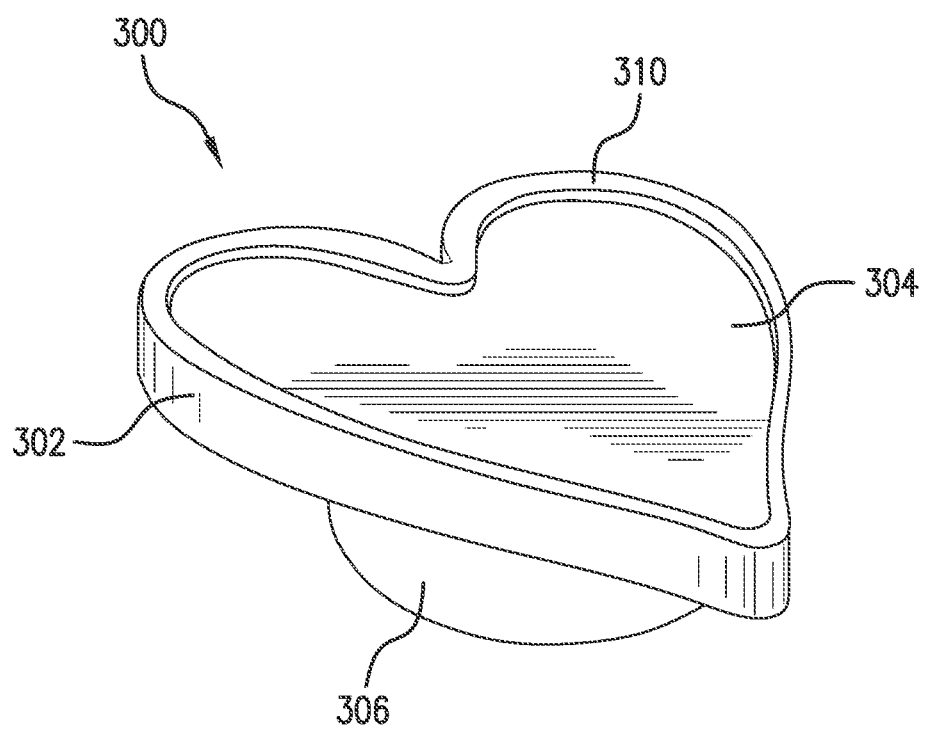
FIG. 3 illustrates a perspective view of an example embodiment of an orthodontic appliance.

FIG. 3 illustrates an example embodiment of an orthodontic appliance 300. Appliance 300 may include a body 302. Body 302 may include a surface 304. Body 302 may be operatively connected to at least one ring-shaped member 306 via at least connecting portion 308. Surface 304 may include a raised element 310.

Body 302 may be substantially planar. Body 302 may be substantially non-planar. Surface 304 may be substantially planar. Surface 304 may be substantially non-planar.

Raised element 310 may be oriented about the edges of a shaped body 302, so as to further define and/or emphasize the shape of body 302. Raised element 310 may include a color different from the remainder of surface 304.

Figure 4A:
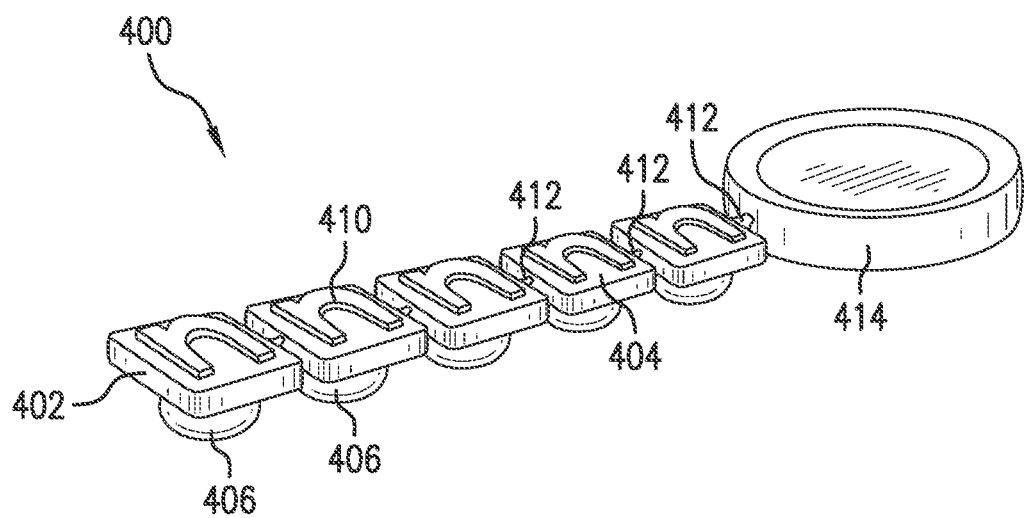
FIG. 4A illustrates a perspective view of an example embodiment of a series of orthodontic appliances as they may be manufactured and/or packaged.
Figure 4B:
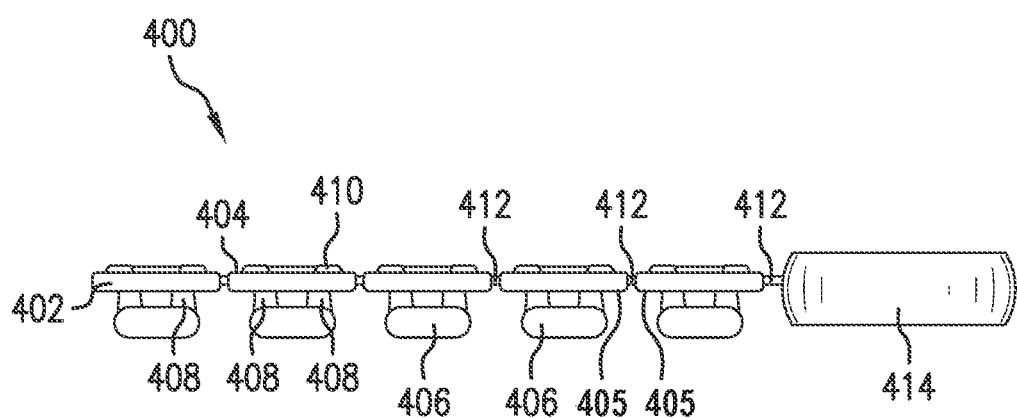
FIG. 4B illustrates an elevational view of an example embodiment of the series of orthodontic appliances as they may be manufactured and/or packaged.

FIGS. 4A and 4B illustrate an example embodiment of a series of orthodontic appliances 400 as they may be manufactured and/or packaged. Appliances 400 may include a body 402. Body 402 may include a surface 404. Body 402 may be operatively connected to at least one ring-shaped member 406 via at least connecting portion 408.

Body 402 may be substantially planar. Body 402 may be substantially non-planar. Surface 404 may be substantially planar. Surface 404 may be substantially non-planar.

Appliances 400 may be formed into a chain, wherein each appliance 400 is adjacent to and connected with another appliance 400 via a link 412. The link 412 may be a very thin portion of material that makes up appliance 400. A user of appliance 400 may simply break off one or more appliance 400 as desired and apply them to a patient, or herself/himself.

Appliances 400 may be formed into a chain having a grasping portion 414 at one end to facilitate easier handling of the chain of appliances 400, for example during removal of one or more appliance 400 therefrom.

Figure 5A:
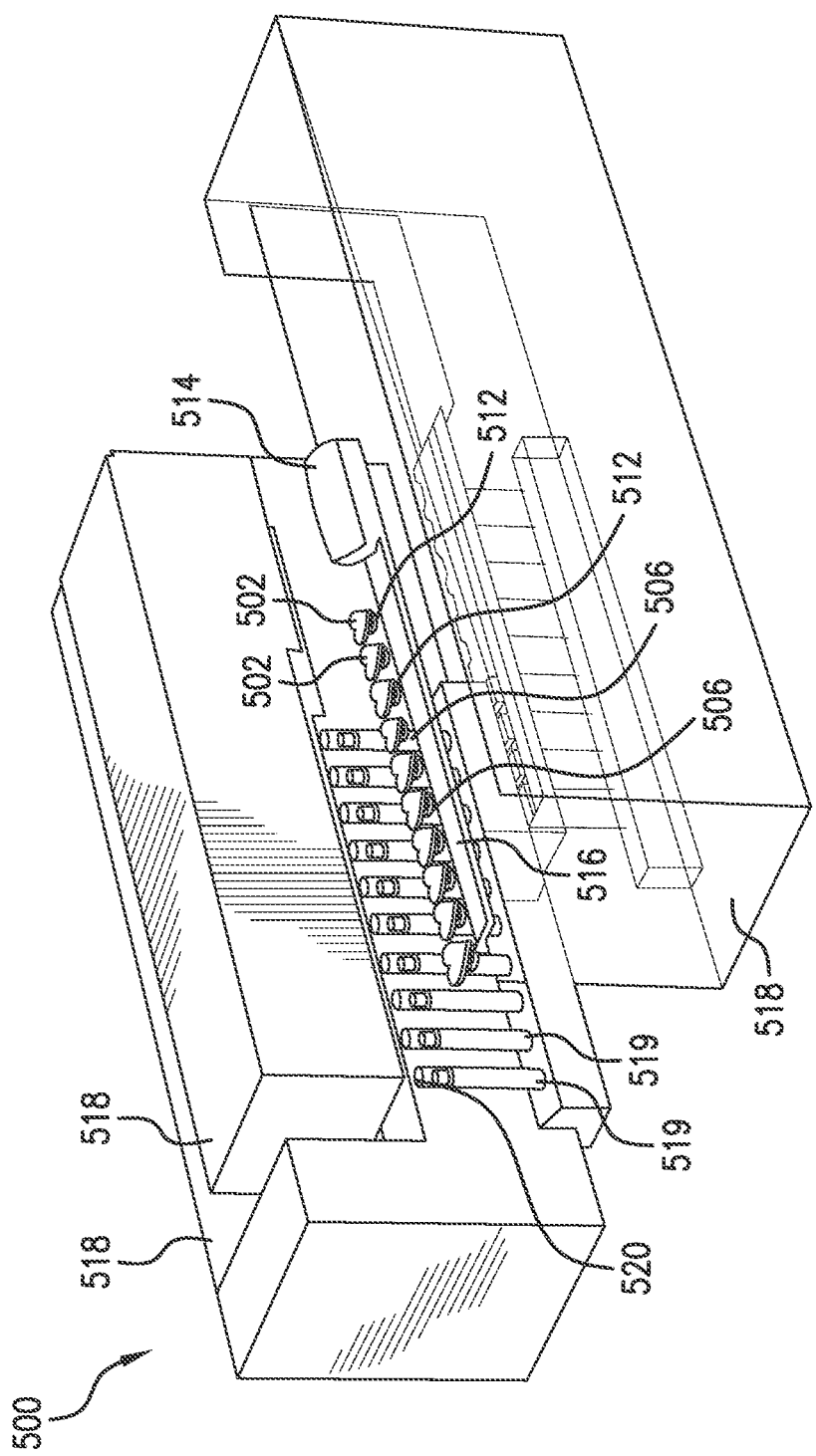
FIG. 5A illustrates a perspective view of an example embodiment of a mold for manufacturing a series of orthodontic appliances.
Figure 5B:
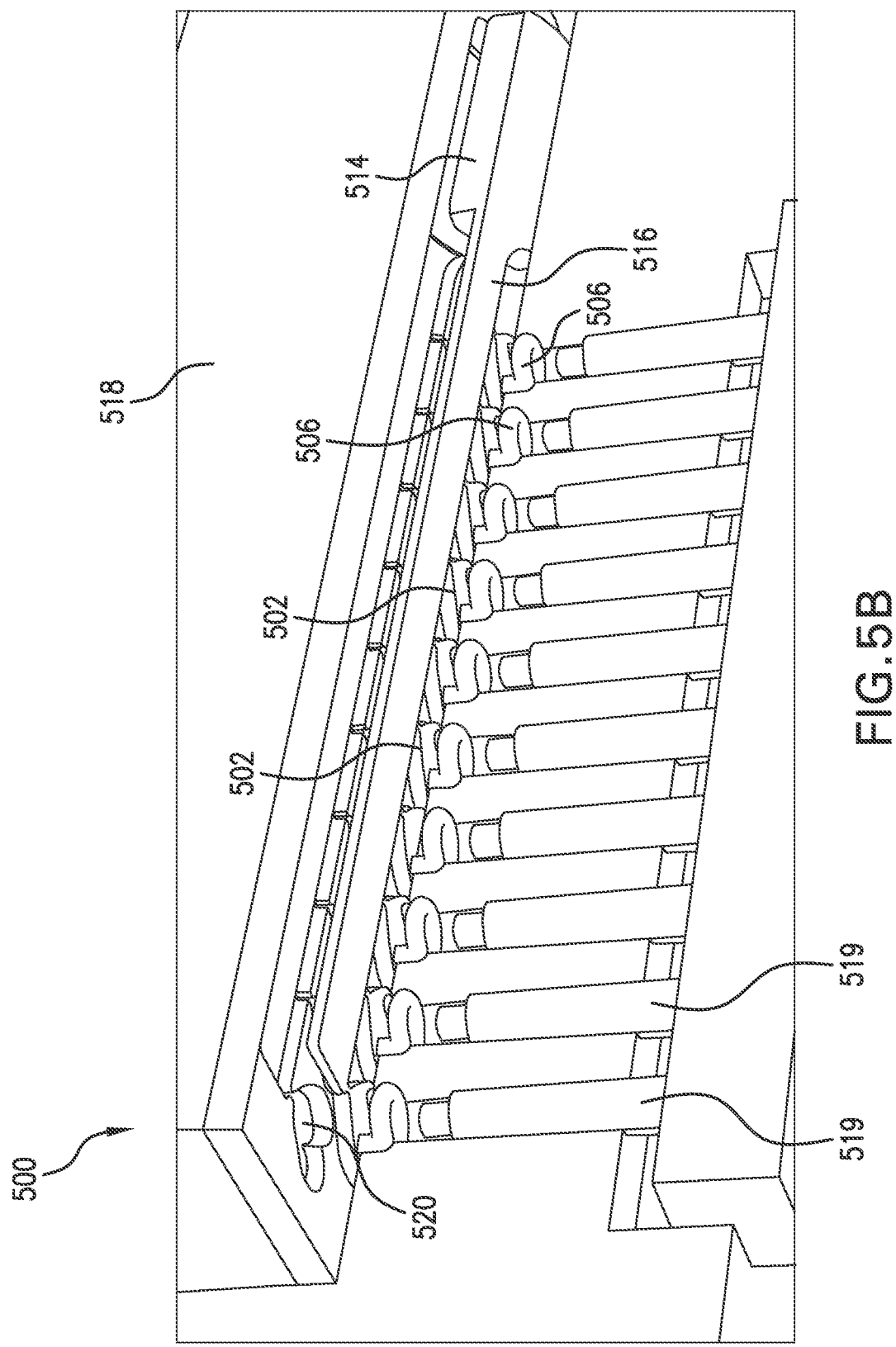
FIG. 5B illustrates a perspective view of an example embodiment of a mold for manufacturing a series of orthodontic appliances.

FIGS. 5A and 5B illustrate an example embodiment of a series of orthodontic appliances 500 as they may be manufactured. Appliances 500 may include a body 502. Body 502 may be operatively connected to at least one ring-shaped member 506 via at least connecting portion (not shown).

Body 502 may be substantially planar. Body 502 may be substantially non-planar.

Appliances 500 may each be connected to a rail 516 configured to support appliances 500 prior to use and installation. Appliances 500 may be connected to rail 516 via very thin links 512. A grasping portion 514 may be connected to rail 516 to facilitate easier handling of the chain of appliances 500, for example during removal of one or more appliance 500 therefrom.

Appliances 500 may be formed, along with rail 516 and grasping portion 514, in a mold 518. Mold 518 may include one or more mold sections. Mold 518 may include at least one mandrel 519. Mold 518 may include mold cavities 520, into which material may be placed (e.g., via injection molding) and cooled or cured as necessary to obtain the desired material properties.

At least one mandrel 519 may include a distal end. The distal end of mandrel 519 may form a hole within ring shaped member 506.

At least one or more section of mold 518 and/or mandrel 519 may be configured to move together into a molding position for forming of appliance 500, and may be configured to move away from one another into an open position for removal of appliance 500 from mold 518.

Figure 6:
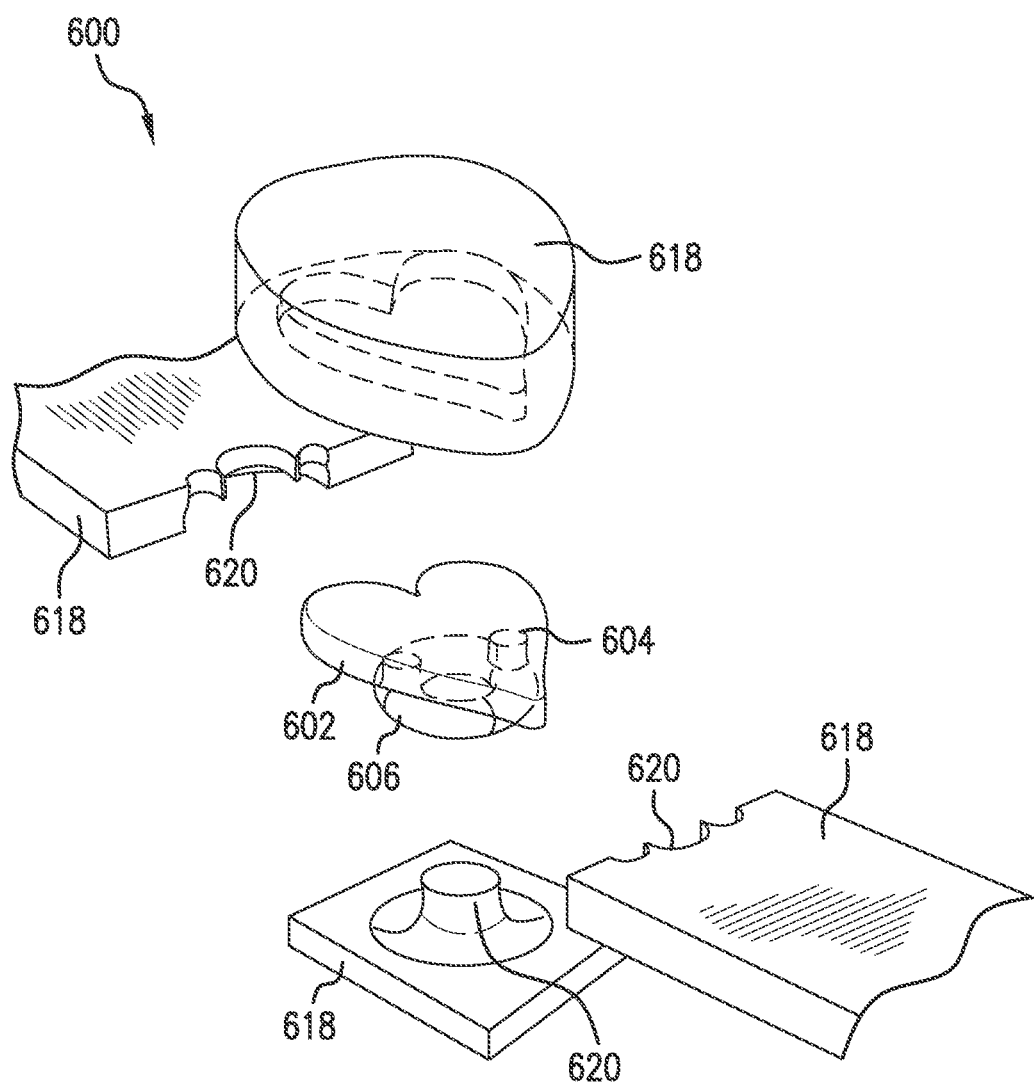
FIG. 6 illustrates a perspective view of an example embodiment of a mold for manufacturing an orthodontic appliance.

FIG. 6 illustrates an example embodiment of an orthodontic appliance 600 and a mold 618 for forming appliance 600. Appliance 600 may include a body 602. Body 602 may include a surface 604. Body 602 may be operatively connected to at least one ring-shaped member 606 via at least one connecting portion (not shown).

Body 602 may be substantially planar. Body 602 may be substantially non-planar. Surface 604 may be substantially planar. Surface 604 may be substantially non-planar.

Mold 618 may include a plurality of mold sections. Mold 618 may include, for example, four mold sections. Mold 618 may include any number of mold sections as required to mold appliance 600. Each mold section may include at least one mold cavity 620. At least one mold cavity 620 may include a negative of the shape of that portion of appliance 600 that is molded in that particular mold cavity 620.

Figure 7A:
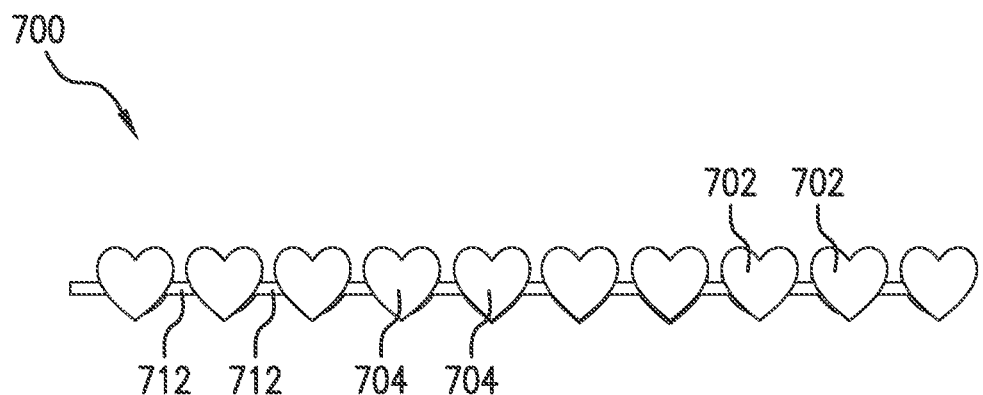
FIG. 7A illustrates a top plan view of an example embodiment of the series of orthodontic appliances as they may be manufactured and/or packaged.
Figure 7B:
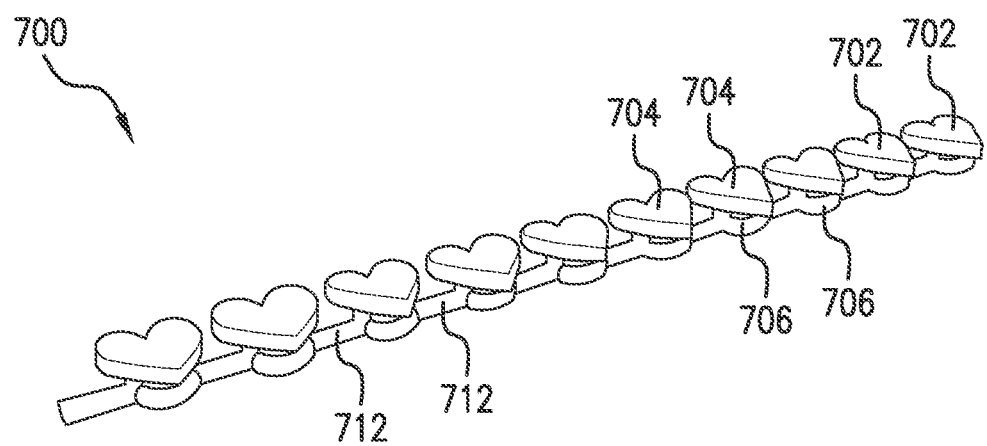
FIG. 7B illustrates a perspective view of an example embodiment of a series of orthodontic appliances as they may be manufactured and/or packaged.

FIGS. 7A and 7B illustrate an example embodiment of the series of orthodontic appliances 700 as they may be manufactured and/or packaged.

Appliances 700 may include a body 702. Body 702 may include a surface 704. Body 702 may be operatively connected to at least one ring-shaped member 706 via at least one connecting portion (not shown). Adjacent appliances 700 may be connected to one another via at least one link 712.

Body 702 may be substantially planar. Body 702 may be substantially non-planar. Surface 704 may be substantially planar. Surface 704 may be substantially non-planar.

Appliances 700 may include a series of appliances that are connected adjacent to one another in a chain. A first appliance may be connected to an adjacent second appliance via link 712. Link 712 may connect to the at least one ring-shaped member 706 of the first appliance and the at least one ring-shaped member 706 of the second appliance. Link 712 may be molded as part of, and thus integrally attached to at least one ring-shaped member 706. Link 712 may be a separate element adhered, welded, extending about, or otherwise attached to and engaged with at least one ring-shaped member 706. Alternatively, link 712 may extend between and connect to at least one connecting portion (not shown). Alternatively, link 712 may extend between and connect to body 702.

A plurality of appliances 700 connected in a chain may be referred to as any of elastomeric chains, energy chains, or power chains. The chain of appliances 700 may be packaged in strips, segments, spools, or the like. In practice, a user may optionally remove individual appliances 700 from the chain and apply them individually to the bracket as noted above. Alternatively, a user may optionally apply two or more appliances 700 still attached via links 712 to adjacent brackets. That is, appliances 700 may remain linked to one another via links 712 after installation onto adjacent brackets.

It may be desirable to apply a chain of appliances 700 to a patient's brackets in order to achieve desired orthodontic mechanics. For example, links 712 between individual appliances 700 may exert additional forces on brackets, and thus teeth, to achieve desired orthodontic mechanics.

In one embodiment, a chain of appliances 700 may be utilized to form a pattern, design, word, numbering scheme, etc. across a series of appliances 700 contained in the chain. For example, each appliance 700 may contain a separate letter, such that when they are oriented adjacent one another in a chain, they form a word. It is contemplated that any pattern of shapes, colors, letters, numbers, indicia, and the like could be formed using a chain of appliances 700.

Figure 8A:
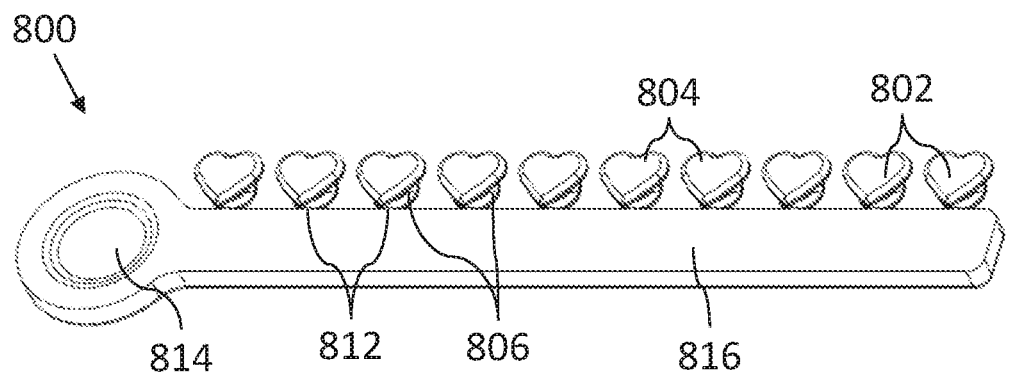
FIG. 8A illustrates a perspective view of an example embodiment of the series of orthodontic appliances as they may be manufactured and/or packaged.
Figure 8B:
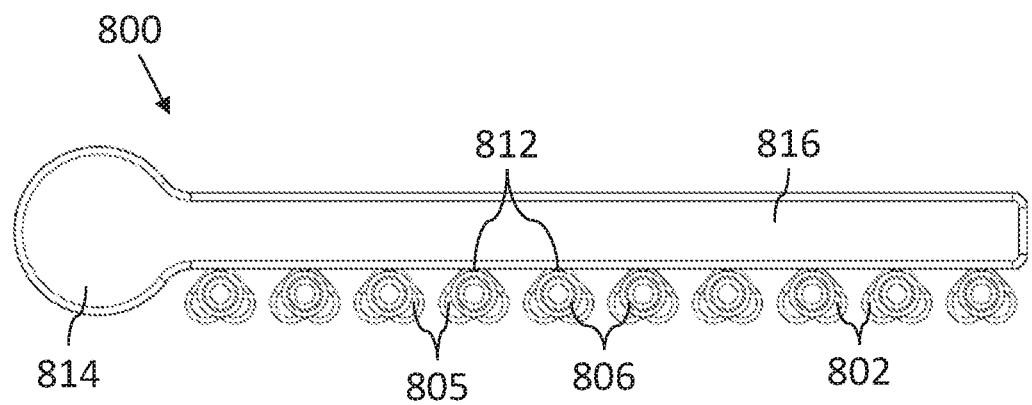
FIG. 8B illustrates a top plan view of an example embodiment of a series of orthodontic appliances as they may be manufactured and/or packaged.
Figure 8C:
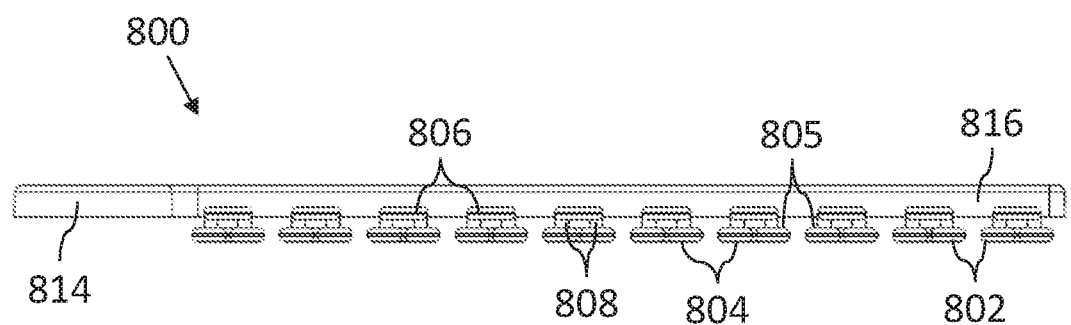
FIG. 8C illustrates an elevational view of an example embodiment of a series of orthodontic appliances as they may be manufactured and/or packaged.

FIGS. 8A, 8B, and 8C illustrate an example embodiment of a series of orthodontic appliances 800 as they may be manufactured. Appliances 800 may include a body 802. Body 802 may be operatively connected to at least one ring-shaped member 806 via at least connecting portion 808.

Body 802 may include a surface 804. Body 802 may include an inner surface 805.

Body 802 may be substantially planar. Body 802 may be substantially non-planar. Surface 804 may be substantially planar. Surface 804 may be substantially non-planar.

Appliances 800 may each be connected to a rail 816 configured to support appliances 800 prior to use and installation. Appliances 800 may be connected to rail 816 via very thin links 812. A grasping portion 814 may be connected to rail 816 to facilitate easier handling of the chain of appliances 800, for example during removal of one or more appliance 800 therefrom.

Grasping portion 814 may include a texture to facilitate easier gripping and/or handling of appliances 800 and rail 816.

Links 812 may be configured to easily break upon a user applying adequate force when pulling appliances 800 from rail 816 prior to installation of appliances 800. Alternatively, links 812 may be cut with a cutting instrument (e.g., scissors, a knife, and the like) in order to separate appliances 800 from rail 816 to permit use of appliances 800. Links 812 may extend between ring-shaped member 806 and rail 816. Links 812 may extend between body 802 and rail 816. Links 812 may extend between any part of appliance 800 and rail 816.

Appliances 800 may be formed, along with rail 816 and grasping portion 814, in a mold (not shown). The mold may be substantially similar to mold 518 illustrated in FIGS. 5A and 5B. Alternatively, the mold may be dissimilar to mold 518.

Figure 9A:
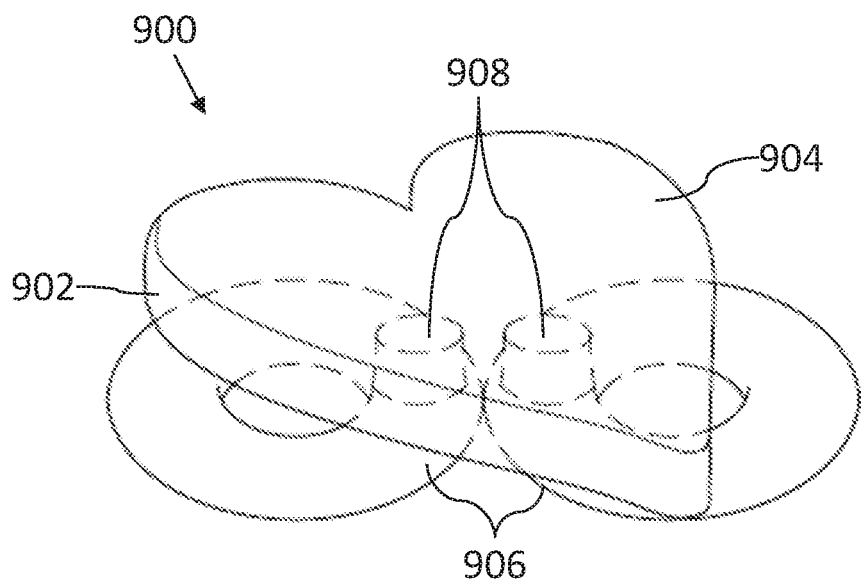
FIG. 9A illustrates a perspective view of an example embodiment of an orthodontic appliance.
Figure 9B:
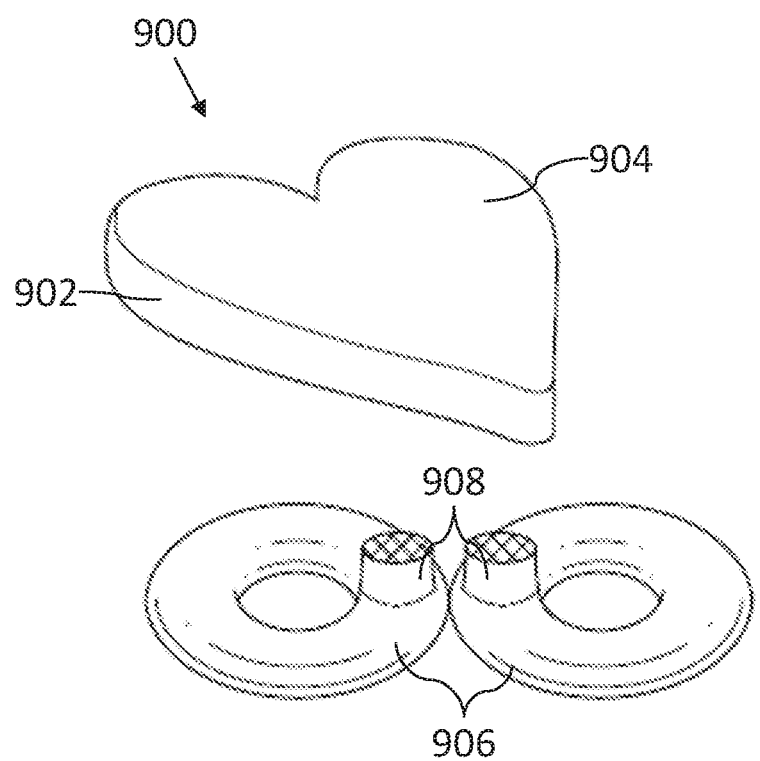
FIG. 9B illustrates an exploded perspective view of an example embodiment of the orthodontic appliance.

FIGS. 9A and 9B illustrate an example embodiment of an orthodontic appliance 900. Appliance 900 may include a body 902. Body 902 may include a surface 904. Body 902 may be operatively connected to at least one ring-shaped member 906 via at least connecting portion 908.

Body 902 may be substantially planar. Body 902 may be substantially non-planar. Surface 904 may be substantially planar. Surface 904 may be substantially non-planar.

As illustrated, appliance 900 may include a plurality of ring-shaped members 906. Body 902 may be operatively connected to each of the plurality of ring-shaped members 906 via at least one connecting portion 908. Body 902 may be operatively connected to each of the plurality of ring-shaped members via one connecting portion 908.

A standard orthodontic bracket comprises four tie wings oriented generally in the shape of a square, with one tie ring at each corner of the square. The tie wings are configured to engage and retain at least one ring-shaped member 906. However, in use, one may place one ring-shaped member 906 about two of the tie wings of the bracket. For example, one may place one ring-shaped member 906 about the upper left and lower left tie wings of the bracket, and one may place a second ring-shaped member 906 about the upper right and lower right tie wings of the bracket. Alternatively, one may place a first ring-shaped member 906 about the upper left and upper right tie wings of the bracket, and a second ring-shaped member 906 about the lower left and lower right tie wings of the bracket. Alternatively, one may place a first ring-shaped member 906 about the upper left and lower right tie wings of the bracket, and a second ring-shaped member 906 about the upper right and lower left tie wings of the bracket.

In another embodiment, appliance 900 may be configured to extend between adjacent brackets, such that body 902 extends between and/or at least partially overlies adjacent brackets. In one embodiment, appliance 900 is configured to application to two adjacent brackets. That is, each of the plurality of ring-shaped members 906 engages one bracket. As illustrated, body 902 may be oriented at least partially diagonally relative to the plurality of ring-shaped members.

Figure 10A:
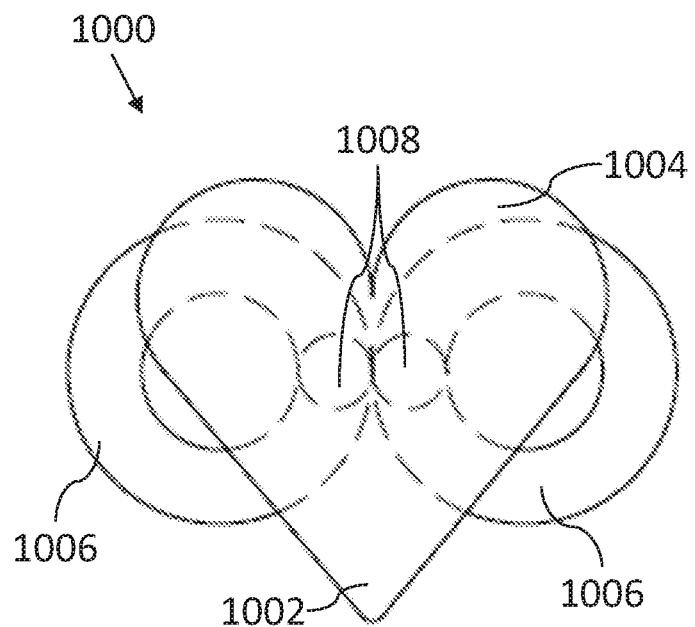
FIG. 10A illustrates a top plan view of an example embodiment of an orthodontic appliance.
Figure 10B:
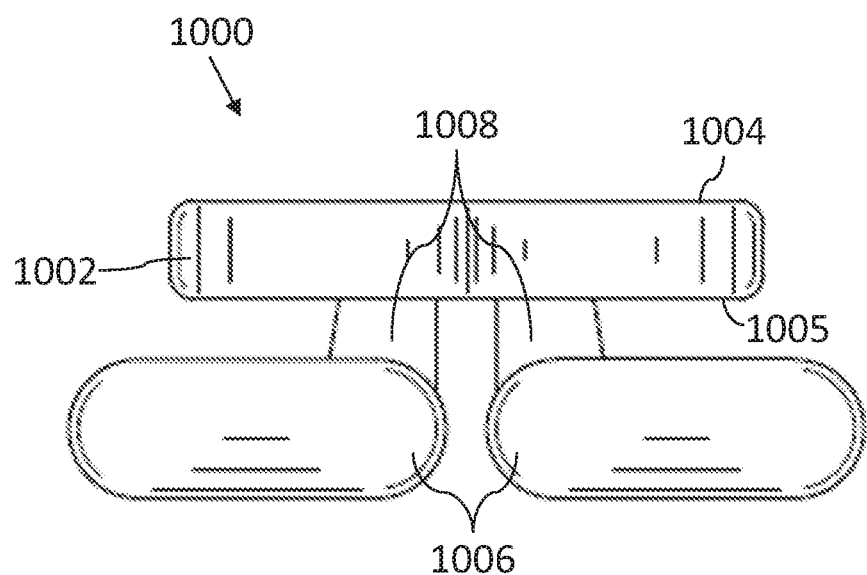
FIG. 10B illustrates an elevational view of an example embodiment of the orthodontic appliance.

FIGS. 10A and 10B illustrate an example embodiment of an orthodontic appliance 1000. Appliance 1000 may include a body 1002. Body 1002 may include a surface 1004. Body 1002 may include an inner surface 1005. Body 1002 may be operatively connected to at least one ring-shaped member 1006 via at least connecting portion 1008.

Body 1002 may be substantially planar. Body 1002 may be substantially non-planar. Surface 1004 may be substantially planar. Surface 1004 may be substantially non-planar.

One may place one ring-shaped member 1006 about the upper left and lower left tie wings of the bracket, and one may place a second ring-shaped member 1006 about the upper right and lower right tie wings of the bracket. Alternatively, one may place a first ring-shaped member 1006 about the upper left and upper right tie wings of the bracket, and a second ring-shaped member 1006 about the lower left and lower right tie wings of the bracket. Alternatively, one may place a first ring-shaped member 1006 about the upper left and lower right tie wings of the bracket, and a second ring-shaped member 1006 about the upper right and lower left tie wings of the bracket.

Alternatively, appliance 1000 may be oriented between adjacent brackets. As illustrated, body 1002 may be oriented substantially vertically relative to the plurality of ring-shaped members, such that body 1002 will be oriented substantially vertically in the plurality of ring-shaped members are applied to adjacent brackets.

Figure 11:
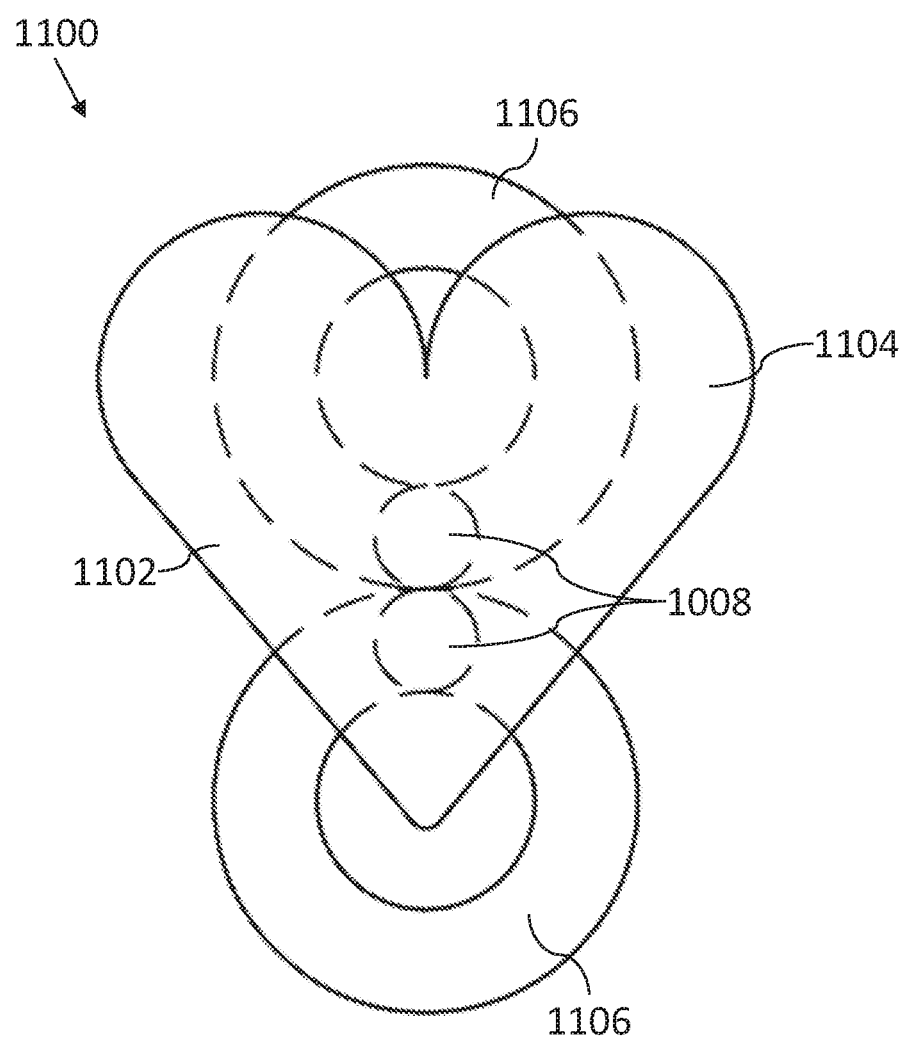
FIG. 11 illustrates a top plan view of an example embodiment of an orthodontic appliance.

FIG. 11 illustrates an example embodiment of an orthodontic appliance 1100. Appliance 1100 may include a body 1102. Body 1102 may include a surface 1104. Body 1102 may be operatively connected to at least one ring-shaped member 1106 via at least connecting portion 1108.

Body 1102 may be substantially planar. Body 1102 may be substantially non-planar. Surface 1104 may be substantially planar. Surface 1104 may be substantially non-planar.

One may place one ring-shaped member 1106 about the upper left and lower left tie wings of the bracket, and one may place a second ring-shaped member 1106 about the upper right and lower right tie wings of the bracket. Alternatively, one may place a first ring-shaped member 1106 about the upper left and upper right tie wings of the bracket, and a second ring-shaped member 1106 about the lower left and lower right tie wings of the bracket. Alternatively, one may place a first ring-shaped member 1106 about the upper left and lower right tie wings of the bracket, and a second ring-shaped member 1106 about the upper right and lower left tie wings of the bracket.

Alternatively, appliance 1100 may be oriented between adjacent brackets. As illustrated, body 1102 may be oriented substantially horizontally relative to the plurality of ring-shaped members, such that body 1102 will be oriented substantially horizontally in the plurality of ring-shaped members are applied to adjacent brackets.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "substantially" is used in the specification or the claims, it is intended to indicate a nature of an element and/or a relationship between elements within a reasonable degree of precision and tolerance as is acceptable in the relevant field of technology. To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. An orthodontic appliance, comprising:
   a body;
   at least one ring-shaped member connected to the body via at least one connecting portion;
   wherein the body and the at least one ring-shaped member are oriented adjacent to one another;
   wherein the body and the at least one ring-shaped member are parallel to one another and lie on separate planes; and
   wherein the at least one connecting portion extends orthogonally to both of the at least one ring-shaped member and the body.

2. The appliance of claim 1, wherein the body includes a surface.

3. The appliance of claim 1, wherein the at least one ring-shaped member is resilient.

* * * * *